(12) United States Patent
Higashide et al.

(10) Patent No.: US 7,189,528 B2
(45) Date of Patent: Mar. 13, 2007

(54) EXTRACT SOLUTION FOR CELL-FREE PROTEIN SYNTHESIS, METHOD FOR CELL-FREE PROTEIN SYNTHESIS USING SAME AND METHOD FOR PREPARATION OF THE EXTRACT SOLUTION

(75) Inventors: Shoken Higashide, Osaka (JP); Toru Ezure, Osaka (JP); Satoko Shiraki, Osaka (JP); Masaaki Ito, Osaka (JP)

(73) Assignee: Shimadzu Corporation, Kyoto (JP)

( * ) Notice: Subject to any disclaimer, the term of this patent is extended or adjusted under 35 U.S.C. 154(b) by 460 days.

(21) Appl. No.: 10/315,108

(22) Filed: Dec. 10, 2002

(65) Prior Publication Data

US 2003/0113836 A1 Jun. 19, 2003

(30) Foreign Application Priority Data

Dec. 10, 2001 (JP) ............................. 2001-375822

(51) Int. Cl.
*C12P 21/06* (2006.01)
(52) U.S. Cl. ..................... 435/68.1; 435/69.1; 435/183; 435/348
(58) Field of Classification Search ............... 435/68.1, 435/69.1, 183, 348
See application file for complete search history.

(56) References Cited

U.S. PATENT DOCUMENTS 5,646,014 A * 7/1997 Hara ........................ 435/69.1

2002/0168705 A1 11/2002 Nunokawa et al.

FOREIGN PATENT DOCUMENTS

JP 2000-236896 9/2000
JP 2000-325076 11/2000

OTHER PUBLICATIONS

Manley et al., "DNA-dependent transcription of adenovirus genes in a soluble whole-cell extract", *Proc. Natl. Acad. Sci. USA*, vol. 77, No. 7, pp. 3855-3859, 1980.
Suzuki et al., "Differential Transcription of the Fibroin and Sericin-1 Genes in Cell-Free Extracts", *Develop. Growth & Differ.*, vol. 32, No. 2, pp. 179-187, 1990.
Murakami et al., "Production of Biologically Active Recombinant Bovine Interferon-γ by Two Different Baculovirus Gene Expression Systems Using Insect Cells and Silkworm Larvae", *Cytokine*, vol. 13, No. 1, pp. 18-24, 2001.

* cited by examiner

*Primary Examiner*—Herbert J. Lilling
(74) *Attorney, Agent, or Firm*—Wenderoth, Lind & Ponack, L.L.P.

(57) ABSTRACT

The present invention provides a novel extract solution for cell-free protein synthesis, which contains at least an extract derived from a *Bombyx mori* L. tissue and an exogenous mRNA, which is easy to prepare and which is capable of realizing cell-free protein synthesis that can synthesize glycoprotein, a cell-free protein synthesis method using it, and a method for preparing an extract solution for cell-free protein synthesis, which includes adding an exogenous mRNA to an extract derived from a *Bombyx mori* L. tissue.

17 Claims, 7 Drawing Sheets

EXTRACT SOLUTION FOR CELL-FREE PROTEIN SYNTHESIS, METHOD FOR CELL-FREE PROTEIN SYNTHESIS USING SAME AND METHOD FOR PREPARATION OF THE EXTRACT SOLUTION

TECHNICAL FIELD OF THE INVENTION

The present invention relates to an extract solution usable for cell-free protein synthesis, a preparation method thereof and a protein synthesis method in a cell-free system using said extract solution.

BACKGROUND OF THE INVENTION

In recent years, genetic information of many organisms including human genome has been decoded. Under the circumstances, functional analysis of proteins corresponding to such genetic information and creation of genomic medicine have been attracting attention as postgenomic studies. Application and utilization of proteins corresponding to such genetic information for pharmaceutical products and the like requires easy syntheses of extensive kinds of proteins in a short time.

At present, expression systems using viable cells (hereinafter sometimes to be referred to as "cell-system") of yeast, insect cell and the like by gene recombination technique have been widely used as the production methods of proteins. However, many proteins are difficult to express. For example, viable cells show a propensity toward elimination of exogenous proteins for their functional retention, and expression of cytotoxic proteins in viable cells prevents cell growth.

As a production method of a protein that does not use a cell-system, a cell-free protein synthesis has been known, which includes adding a substrate, enzyme and the like to a cell rupture and extract solution and the like to provide a wide choice of genetic information translation systems of organism in test tubes, and reconstructing a synthetic system capable of linking the necessary number of residues in a desired order of amino acids using an mRNA encoding the objective protein. Such a cell-free protein synthesis is not easily limited unlike the above-mentioned cell-system protein synthesis, and proteins can be synthesized without killing the organism. In addition, because the production of protein does not accompany operations such as cultivation and the like, a protein can be synthesized in a short time as compared to cell-systems. Moreover, inasmuch as the cell-free protein synthesis also affords a large-scale production of proteins consisting of the amino acid sequence that the organism does not use, it is expected to be a promising expression method. As such cell-free protein synthesis, for example, methods using an extract solution of wheat germ and that of *Escherichia coli* have been known.

In a cell-free protein synthesis using an extract solution of wheat germ, however, the extraction process for the extract solution is generally extremely complicated.

As one example of the preparation method of an extract solution of wheat germ, JP-A-2000-236896 describes the following steps. Wheat seeds are added in a mill, ruptured and a crude germ fraction is obtained using a sieve. By flotation with a mixture of carbon tetrachloride and cyclohexane (carbon tetrachloride:cyclohexane=2.5:1), germinative embryo is recovered from the floating fractions and the organic solvent is removed by drying at room temperature. The impurities contained in the embryo fraction, such as seed coat and the like, are removed by adsorption using a static electricity charged body. Then, to completely remove a wheat albumen component from this sample, it is suspended in a 0.5% solution of NP40, a nonionic detergent, and repeatedly washed with an ultrasonic cleaner until the washing does not become cloudy. Ultrasonic cleaning is done once again in the presence of distilled water to purify the wheat germ.

The cell-free protein synthesis using an extract solution of wheat germ in this way requires complicated preparation of an extract solution, inconveniently demanding long hours and much labor.

A cell-free protein synthesis using an extract solution of *Escherichia coli* fails in glycosylation to a protein, because *Escherichia coli* is a procaryote, and cannot synthesize glycoprotein. The sugar chain added to a protein by the above-mentioned glycosylation is considered to function as a function regulating factor of a protein itself or a protective and stabilizing factor of protein, in the form of a signal or ligand involved in the recognition and adhesion between substances or between cells. For the analysis of in vivo function of a protein to be glycosylated, a glycosylated protein (glycoprotein) should be obtained. Thus, there is a demand for a cell-free protein synthesis that permits glycosylation after translation into a protein.

SUMMARY OF THE INVENTION

The present invention has been made to solve the above-mentioned problems and provides a novel extract solution for cell-free protein synthesis, which is easy to prepare and realizes a cell-free protein synthesis permitting synthesis of a glycoprotein, a preparation method thereof, and a protein synthesis method in a cell-free system using the extract solution.

As a result of the intensive studies conducted by the present inventors in an attempt to solve the above-mentioned problems, it has been found that an extract solution containing at least an extract derived from a *Bombyx mori* L. tissue and an exogenous mRNA is easy to prepare, and that cell-free protein synthesis using the solution affords synthesis of a large amount of protein, which resulted in the completion of the present invention.

Accordingly, the present invention provides the following.

(1) An extract solution for cell-free protein synthesis, which contains at least an extract derived from a *Bombyx mori* L. tissue and an exogenous mRNA.

(2) The extract solution of the above-mentioned (1), which further contains a protease inhibitor.

(3) The extract solution of the above-mentioned (1) or (2), wherein a content of the extract derived from a *Bombyx mori* L. tissue is 1 mg/mL-200 mg/mL in a protein concentration.

(4) The extract solution of any of the above-mentioned (1) to (3), wherein the *Bombyx mori* L. tissue contains at least the posterior silk gland of *Bombyx mori* L. larva.

(5) The extract solution of any of the above-mentioned (1) to (3), wherein the *Bombyx mori* L. tissue contains at least a fat body of *Bombyx mori* L. larva.

(6) The extract solution of any of the above-mentioned (1) to (3), wherein the *Bombyx mori* L. tissue contains at least an embryo of *Bombyx mori* L.

(7) The extract solution of any of the above-mentioned (2) to (6), wherein the protease inhibitor is phenylmethanesulfonyl fluoride.

(8) A liquid composition for cell-free protein synthesis, which contains at least an extract derived from a *Bombyx mori* L. tissue and a protease inhibitor.
(9) A method for cell-free protein synthesis using the extract solution of any of the above-mentioned (1) to (7).
(10) A method for preparing an extract solution for cell-free protein synthesis, which comprises adding an exogenous mRNA to an extract derived from a *Bombyx mori* L. tissue, which was extracted from a *Bombyx mori* L. tissue using a solution for extraction.
(11) The preparation method of the above-mentioned (10), wherein the solution for extraction contains at least a protease inhibitor.
(12) The preparation method of the above-mentioned (10) or (11), wherein the extract derived from a *Bombyx mori* L. tissue, which was extracted from a *Bombyx mori* L. tissue using a solution for extraction is subjected to a treatment for removing a liquid fibroin.

DETAILED DESCRIPTION OF THE INVENTION

Figure 1:
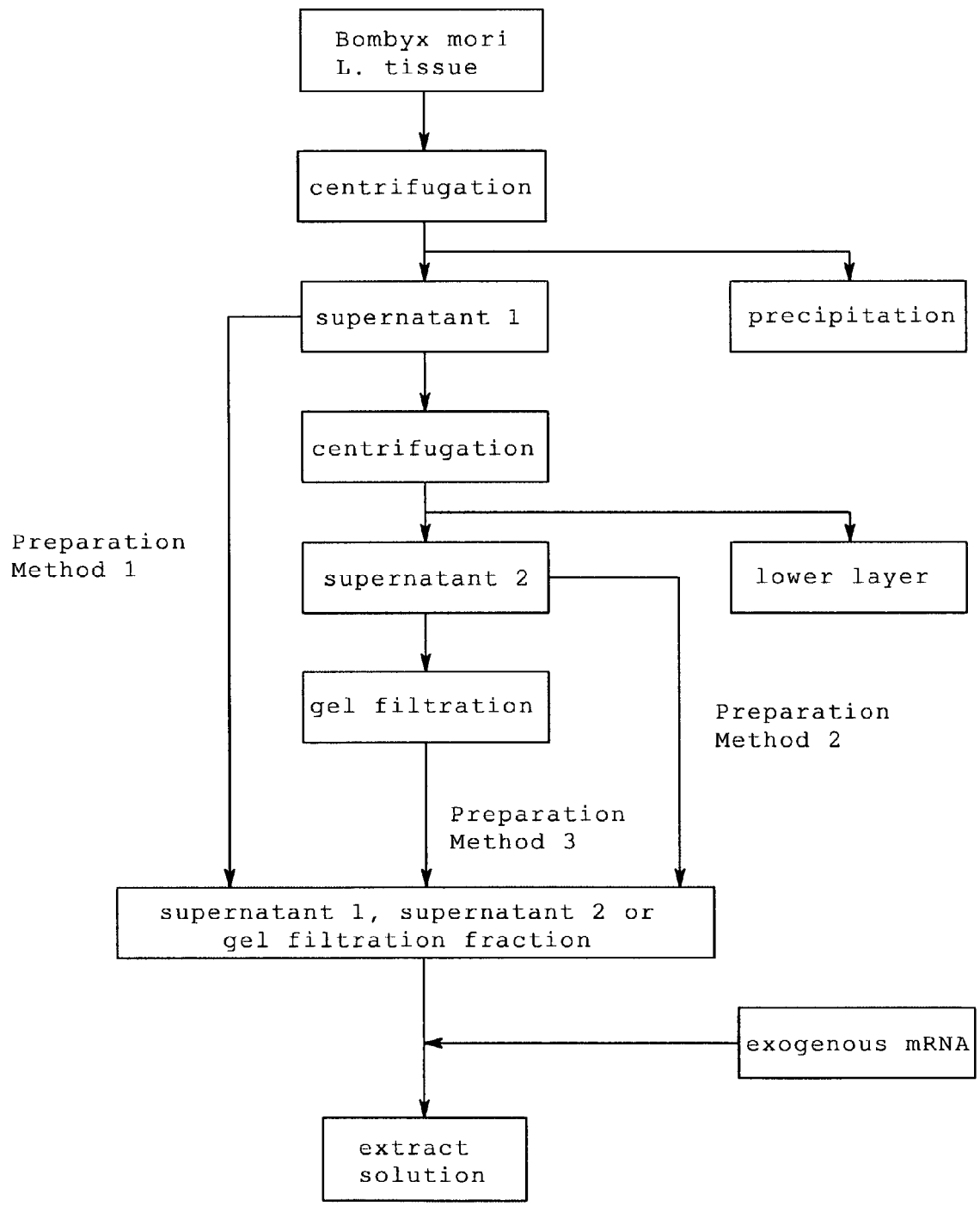
FIG. 1 is a flow chart showing preparation methods 1–3 of the extract solution of the present invention in a simplified manner.

In the present specification, the "*Bombyx mori* L." means Lepidoptera belonging to Bombycidae. In its life, it goes through the stages of "embryo" (from immediately after oviposition to immediately before hatching), "larva" (from immediately after hatch to immediately before completion of formation of cocoon (laraval stage 1–laraval stage 5)), "pupae" (from immediately before completion of formation of cocoon to immediately before eclosion), and "imago" (from immediately after eclosion to death), and "*Bombyx mori* L." includes any stage over its lifetime.

*Bombyx mori* L. in the stage of larva after hatching of the egg alternately repeats the period of eating Mulberry to grow (instar) and the period of getting ready for moult without eating (moulting). In the larva of *Bombyx mori* L., the period of from hatching to the first moult is called laraval stage 1, and that from the 1st moult to the 2nd moult is called laraval stage 2, and the larva generally gets matured after 4 times of moult and in laraval stage 5 (*Bombyx mori* L. larva in the matured state is also called a "mature larva"). The mature larva of *Bombyx mori* L. has a transparent body, expectorates a silk thread to form a cocoon for pupation. After pupae, it ecloses into an imago.

The "silk gland" in the present specification refers to a pair of tubular exocrine glands which continue from spinneret located on the tip of labium on the head to culdesac on both sides of the body of *Bombyx mori* L. larva, and is roughly divided into an anterior silk gland, a middle silk gland and a posterior silk gland. The posterior silk gland secretes fibroin that constitutes the center portion of silk. The middle silk gland secretes sericin. The fibroin is accumulated in the middle silk gland and coated with sericin on the outer periphery, and forms a gel silk substance. This silk substance is discharged from spinneret through anterior silk gland and solidified to give silk.

The "fat body" in the present specification is distributed in any part of the body of *Bombyx mori* L. larva and is a white soft and flat band, belt or leaf tissue. Since fat body stores nutrition and energy source like human liver, the cell contains various substances related to the metabolism such as fat drop, protein, glycogen and the like.

The "embryo" in the present specification means a tissue of *Bombyx mori* L. in the state of egg.

The "cell-free protein synthesis" in the present specification means a protein synthesis using a cell-free translation system to synthesize a protein by reading the information of mRNA. As used herein, the "protein" synthesized in the cell-free system by the synthesis method of the present invention encompasses any peptide having any molecular weight, which consists of plural amino acid residues, i.e., from low molecular weight peptides to high molecular weight peptides. The "protein" in the present specification includes glycosylated glycoprotein.

EMBODIMENT OF THE INVENTION

The present invention is explained in detail in the following.

An "extract derived from a *Bombyx mori* L. tissue" in the extract solution of the present invention may be derived from a tissue of *Bombyx mori* L. in any stage of its life (embryo, larva (laraval stage 1–laraval stage 5), pupae, imago). The *Bombyx mori* L. tissue is not limited to a single tissue in a single state (e.g., only posterior silk gland in laraval stage 5 of *Bombyx mori* L. larvae), but may be derived from plural tissues in a single state (e.g., posterior silk gland and fat body of *Bombyx mori* L. larvae of laraval stage 5), or a single tissue in plural states (e.g., posterior silk gland of *Bombyx mori* L. larvae in each of laraval stage 3, laraval stage 4 and laraval stage 5). It is needless to say that it may be derived from plural tissues in plural states.

The above-mentioned "extract derived from a *Bombyx mori* L. tissue" does not need to be an extract from the entirety of the tissue of *Bombyx mori* L. (e.g., entire posterior silk gland).

The content of an extract derived from a *Bombyx mori* L. tissue in the extract solution of the present invention is free of any particular limitation, but it is preferably 1 mg/mL–200 mg/mL, more preferably 10 mg/mL–100 mg/mL, in a protein concentration. When the content of the extract is less than 1 mg/mL in a protein concentration, the concentration of the components essential for the action of the present invention becomes low and possibly prevents sufficient synthetic reaction, and when the content of the extract exceeds 200 mg/mL in protein concentration, the extract solution itself has a high viscosity and makes operations difficult.

An extract solution containing the above-mentioned amount of an extract derived from a *Bombyx mori* L. tissue can be prepared utilizing the measurement of the protein concentration of the extract solution. The measurement of the protein concentration is conducted using a BCA Protein assay Kit (manufactured by PIERCE) by, for example, adding 0.1 mL of a sample to a reaction reagent (2 mL), reacting the mixture at 37° C. for 30 min and measuring the absorbance at 562 nm, as generally done in this field. As a control, bovine serum albumin (BSA) is generally used.

The above-mentioned *Bombyx mori* L. tissue is desirably at least one selected from posterior silk gland of *Bombyx mori* L. larva, fat body of *Bombyx mori* L. larva and embryo of *Bombyx mori* L. Whether or not an extract derived from at least the posterior silk gland of *Bombyx mori* L. larva, fat body of *Bombyx mori* L. larva and embryo of *Bombyx mori* L. is contained in an extract solution can be determined by, for example, an isozyme analysis of aldolase (Nagaoka et al., (1995), Insect Biochem Mol Biol. 25, 819–825).

It is preferable that at least an extract derived from the posterior silk gland of *Bombyx mori* L. larvae be contained, because an extract solution for cell-free protein synthesis having a particularly superior advantage, that a large amount of protein can be synthesized in a short time, can be afforded.

An extract of a fat body derived from *Bombyx mori* L. larva is preferable because an extract solution for cell-free protein synthesis can be realized, which has a particularly superior advantage that a fat body consisting of soft tissues can be mashed in a short time, as a result of which an extract solution can be easily prepared. Whether or not a fat body is contained in an extract solution can be determined by, besides the above-mentioned isozyme analysis, detecting SP-1, SP-2 and the like, which are proteins derived from a fat body, by applying the extract solution to sodium dodecyl sulfate-polyacrylamide gel electrophoresis (SDS-PAGE).

An extract derived from embryo of *Bombyx mori* L. is preferable because an extract solution for cell-free protein synthesis can be realized, which has a particularly superior advantage that, because an embryo is a single individual, a step for enucleation is not necessary, unlike other tissues, as a result of which an extract solution can be prepared easily. Whether or not an embryo of *Bombyx mori* L. is contained in an extract solution can be determined by, besides the above-mentioned isozyme analysis, detecting 30K, ESP, Vitellin(H), Vitellin(L) and the like, which are proteins derived from an embryo, by applying the extract solution to sodium dodecyl sulfate-polyacrylamide gel electrophoresis (SDS-PAGE).

When the extract is derived from the posterior silk gland or fat body of *Bombyx mori* L. larva, any of laraval stage 1–laraval stage 5 of *Bombyx mori* L. larvae can be used for the present invention without any particular limitation. The posterior silk gland and fat body are preferably derived from *Bombyx mori* L. larvae in laraval stage 5. This has an advantage because the posterior silk gland and fat body of *Bombyx mori* L. larva in laraval stage 5 are the most mature from among those in laraval stage 1–laraval stage 5, and the use thereof enables synthesis of a large amount of protein in a short time as compared to synthesis using larvae in other laraval stages.

Particularly, the extract solution of the present invention preferably contains the posterior silk gland of *Bombyx mori* L. larvae in laraval stage 5, particularly an extract of the posterior silk gland of *Bombyx mori* L. larvae at day 3–day 7 of laraval stage 5, as an essential component, because silk fibroin, which is a main component of silk, is actively made and the *Bombyx mori* L. larva in this period has high protein synthesis capability.

In the extract solution of the present invention, moreover, exogenous mRNA is contained as an essential component along with the above-mentioned extract derived from a *Bombyx mori* L. tissue. As used herein, by the "exogenous mRNA" is meant an mRNA not derived from a *Bombyx mori* L. tissue. As long as it is not derived from a *Bombyx mori* L. tissue, the protein (including peptide) to be encoded thereby is not particularly limited, and it may encode a protein having toxicity, or may encode a glycoprotein. Whether mRNA contained in the extract solution is an exogenous mRNA or an mRNA derived from *Bombyx mori* L. tissue can be determined by, after isolation and purification of mRNA from an extract solution, synthesizing cDNA by a reverse transcriptase, analyzing a base sequence of the obtained cDNA, and comparing with a base sequence of known exogenous mRNA.

The exogenous mRNA to be used in the present invention is not particularly limited as regards the number of bases thereof, and the whole mRNA does not need to contain the same number of bases as long as the objective protein can be synthesized. In addition, each mRNA may have plural bases that are deleted, substituted, inserted or added as long as they are homologous sequences capable of synthesizing the objective protein.

The extract solution preferably contains 1 μg/mL–10 mg/mL, more preferably 15 μg/mL–1700 μg/mL, of the exogenous mRNA, in view of the speed of the protein synthesis. When the amount of the exogenous mRNA is less than 1 μg/mL, the mRNA becomes unstable in the extract solution, and when it exceeds 10 mg/mL, viscosity becomes high to make operability poor. When the amount of the exogenous mRNA is less than 1 μg/mL or above 10 mg/mL, the speed of protein synthesis using this mRNA tends to become lower.

By conducting a protein synthesis reaction using such an extract solution containing an extract derived from a *Bombyx mori* L. tissue and an exogenous mRNA, any protein, even if a protein that becomes cytotoxic in viable cell, can be synthesized in a short time. In addition, because an extract derived from eucaryotic *Bombyx mori* L. is used, a glycoprotein can be synthesized in a cell-free system, and various kinds of proteins can be synthesized without particular limitation.

Moreover, according to the present invention, an extract solution, which can be applied to such cell-free protein synthesis, can be prepared strikingly easily as compared to conventional preparation of an extract solution from wheat germ, and efficient cell-free protein synthesis can be realized.

The extract solution of the present invention preferably contains a protease inhibitor, in addition to the above-mentioned extract derived from a *Bombyx mori* L. tissue and exogenous mRNA. By the presence of a protease inhibitor, the preparation is facilitated and a protein (including glycoprotein) can be synthesized efficiently, and an extract solution extremely useful for a protein synthesis in a cell-free system can be provided. This is considered to be attributable to the fact that the activity of protease contained in an extract derived from a *Bombyx mori* L. tissue can be inhibited by a protease inhibitor, and an undesirable decomposition of an active protein in an extract by the protease can be prevented, as a result of which a protein synthesis capability that an extract derived from a *Bombyx mori* L. tissue has can be effectively elicited.

Such protease inhibitor is not particularly limited as long as it can inhibit the activity of protease, and, for example, phenylmethanesulfonyl fluoride (hereinafter sometimes to be referred to as "PMSF"), aprotinin, bestatin, leupeptin, pepstatin A, E-64 (L-trans-epoxysuccinyl-L-leucylamido(4-guanidino)butane), ethylenediaminetetraacetic acid, phosphoramidon and the like can be used. Because an extract solution derived from *Bombyx mori* L. tissue contains serine protease, the use of PMSF, which works as an inhibitor having high specificity to serine protease, is preferable among those mentioned above.

It is possible to use not only one kind of a protease inhibitor but also a mixture (protease inhibitor cocktail) of several kinds of protease inhibitors.

The content of the protease inhibitor in an extract solution is free of any particular limitation, but it is preferably 1 µM–50 mM, more preferably 0.01 mM–5 mM, because decomposition of the enzymes necessary for the action of the present invention can be preferably inhibited. This is because the decomposition activity of protease cannot be sufficiently suppressed when the protease inhibitor is less than 1 µM, and the protein synthesis reaction tends to be inhibited when the protease inhibitor exceeds 50 mM.

The extract solution of the present invention preferably contains, in addition to the above-mentioned extract, an exogenous mRNA and a protease inhibitor, at least a potassium salt, a magnesium salt, a dithiothreitol and a buffer. This has a consequence that an extract solution for cell-free protein synthesis that can advantageously stably maintain components essential for the action of the present invention can be realized.

The above-mentioned potassium salt is free of any particular limitation as long as it does not inhibit the action of the present invention, and can be used in a general form, such as potassium acetate, potassium carbonate, potassium hydrogen carbonate, potassium chloride, dipotassium hydrogen phosphate, dipotassium hydrogen citrate, potassium sulfate, potassium dihydrogen phosphate, potassium iodide, potassium phthalate and the like, with preference given to potassium acetate.

The content of potassium salt in the extract solution is free of any particular limitation, but from the aspect of preservation stability, it is preferably 10 mM–500 mM, more preferably 50 mM–200 mM, in the case of monovalent potassium salt, such as potassium acetate and the like. When the content of potassium salt is less than 10 mM or more than 500 mM, the components essential for protein synthesis tend to be unstable.

The above-mentioned magnesium salt is free of any particular limitation as long as it does not inhibit the action of the present invention, and can be used in a general form such as magnesium acetate, magnesium sulfate, magnesium chloride, magnesium citrate, magnesium hydrogen phosphate, magnesium iodide, magnesium lactate, magnesium nitrate, magnesium oxalate and the like, with preference given to magnesium acetate. Magnesium salt also acts as a cofactor in the protein synthesis reaction.

The content of magnesium salt in the extract solution is free of any particular limitation, but from the aspect of preservation stability, it is preferably 0.1 mM–10 mM, more preferably 0.5 mM–5 mM, in the case of divalent salt, such as magnesium acetate, and the like. When the content of magnesium salt is less than 0.1 mM or more than 10 mM, the components essential for protein synthesis tend to become unstable.

The above-mentioned dithiothreitol (hereinafter sometimes to be referred to as "DTT") is added for prevention of oxidization, and is preferably contained in an amount of 0.1 mM–10 mM, more preferably 0.5 mM–5 mM, in the extract solution. When the content of DTT is less than 0.1 mM or more than 10 mM, the components essential for protein synthesis tend to become unstable.

The above-mentioned buffer imparts a buffer capacity to an extract solution, and is added for the prevention of denaturation of an extract caused by radical change in pH of an extract solution due to the addition of an acidic or basic substance and the like. Such buffer is free of any particular limitation, and, for example, HEPES-KOH, Tris-HCl, acetic acid-sodium acetate, citric acid-sodium citrate, phosphoric acid, boric acid, MES, PIPES and the like can be used.

The buffer is preferably one that maintains the pH of the extract solution at 4–10, more preferably pH 6–8. When the pH of the extract solution is less than 4 or more than 10, the components essential for the reaction of the present invention may be denatured. From this aspect, the use of HEPES-KOH (pH 6–8) is particularly preferable among the above-mentioned buffers.

While the content of the buffer in the extract solution is free of any particular limitation, it is preferably 5 mM–200 mM, more preferably 10 mM–50 mM, to maintain preferable buffer capacity. When the content of the buffer is less than 5 mM, pH may change radically due to the addition of an acidic or basic substance, which in turn may cause denaturation of the extract, and when the content of the buffer exceeds 200 mM, the salt concentration becomes too high and the components essential for protein synthesis tend to become unstable.

That is, the extract solution of the present invention is preferably realized to contain at least one extract from the posterior silk gland, fat body and embryo, in a protein concentration of 1 mg/mL–200 mg/mL, 1 µg/mL–10 mg/mL of exogenous mRNA, 10 mM–500 mM of potassium acetate, 0.1 mM–10 mM of magnesium acetate, 0.1 mM–10 mM of DTT, 1 µM–50 mM of PMSF, and 5 mM–200 mM of HEPES-KOH (pH 6–8).

The present invention also provides a novel preparation method of an extract solution for cell-free protein synthesis.

The preparation method of the extract solution of the present invention includes adding an exogenous mRNA to an extract derived from a *Bombyx mori* L. tissue, which was extracted from a *Bombyx mori* L. tissue using a solution for extraction, to give an extract solution. According to the preparation method of the extract solution of the present invention, at least a treatment for extraction from a *Bombyx mori* L. tissue is contained, and preferably, purification is conducted after extraction from the *Bombyx mori* L. tissue. Specific steps include the following.

First, according to the conventional method, for example, a desired tissue is removed from *Bombyx mori* L. using a tool such as scissors, pincette, scalpel and the like. The amount of the tissue to be used for the extraction to be mentioned below, which was obtained by this removal, is free of any particular limitation, but it is generally in the range of 1 g–100 g. Then, the removed tissue is frozen with, for example, liquid nitrogen, mashed in a mortar frozen at −80° C., and extracted with a solution for extraction. As the solution for extraction to be used here can be a conventionally known buffer solution generally used for extraction, but preferably one containing a protease inhibitor, a potassium salt, a magnesium salt, DTT and a buffer. Particularly preferably, a solution for extraction containing 0.01 mM–5 mM of PMSF, 50 mM–200 mM of potassium acetate, 0.5 mM–5 mM of magnesium acetate, 0.5 mM–5 mM of DTT and 10 mM–50 mM of HEPES-KOH (pH 6–8) is obtained.

In this way, a liquid containing an extract from a tissue of *Bombyx mori* L. is used.

Then, the liquid obtained by the above-mentioned extraction treatment is applied to centrifugal separation. The centrifugal separation is performed under the conditions generally employed in this field (10000×g–50000×g, 0° C.–10° C., 10 min–60 min). According to the preparation method of the present invention, a supernatant after centrifugal separation once (hereinafter to be referred to as "supernatant 1") is used as it is, and an exogenous mRNA may be added to give an extract solution (hereinafter to be referred to as "preparation method 1"), or the supernatant is again applied to the centrifugal separation under the above-mentioned conditions and an exogenous mRNA may be added to the obtained supernatant (hereinafter to be referred to as "supernatant 2") (hereinafter to be referred to as "preparation method 2"). The centrifugal separation to be applied again is preferably a step for separation of liquid fibroin, which is particularly problematic when silk gland is used as a *Bombyx mori* L. tissue, and the conditions of centrifugal separation are preferably set to achieve the object. In view of the possibility of the components (e.g., ribosome, aminoacyl tRNA synthetase, various translation factors and the like) in the *Bombyx mori* L. tissue, which are essential for the protein synthesis reaction, being taken into the liquid fibroin, the separation step is a useful treatment. The liquid fibroin is present in a lower layer obtained by the centrifugal separation to be applied again. Alternatively, the supernatant obtained by the above-mentioned centrifugal separation(s) is(are) subjected to gel filtration, the filtrate after gel filtration is applied to a treatment to separate a fraction having an absorbance at 280 nm of not less than 10 and an exogenous mRNA may be added to the obtained liquid (hereinafter to be referred to as "preparation method 3"). FIG. 1 is a flow chart showing the preparation methods 1–3 of the above in a simplified manner.

When the above-mentioned preparation method 3 is performed, the following steps are specifically conducted.

The supernatant after centrifugal separation is first applied to gel filtration, wherein, as the gel filtration, for example, desalting column PD-10 (manufactured by Amersham Biosciences) can be preferably used. According to a conventional method, the column is equilibrated with a buffer solution for gel filtration, a sample is fed, and the mixture is eluted with the above-mentioned solution for extraction. The above-mentioned buffer solution for gel filtration is preferably the above-mentioned solution for extraction supplemented with glycerol. Using this, the components essential for protein synthesis are beneficially stabilized. Glycerol only need to be added at generally 5(v/v)%–40(v/v)% (preferably 20(v/v)%).

The filtrate (0.1 mL–1 mL) obtained by gel filtration is used as one fraction, as in general gel filtration, and 0.4 mL–0.6 mL is preferably used as one fraction for efficient separation of fraction having high protein synthesis capability.

Then, a fraction showing an absorbance at 280 nm of not less than 10 is separated from the filtrate after gel filtration. This step includes, for example, measurement of the above-mentioned absorbance at 280 nm of each fraction using instruments such as Ultrospec 3300pro (manufactured by Amersham Biosciences) and the like and separation of fraction(s) having the absorbance of not less than 10. An exogenous mRNA is added to the fraction(s) obtained in this way to give the extract solution of the present invention. The extract solution of the present invention may naturally be one that is obtained by adding an exogenous mRNA to a mixture of plural fractions having the above-mentioned absorbance at 280 nm of not less than 10.

The extract solution of the present invention is preferably prepared by the following preparation method containing a step for removing liquid fibroin (hereinafter to be referred to as "preparation method 4") to achieve an extract solution having higher protein synthesis capability. When liquid fibroin is contained in an extract solution, this liquid fibroin itself may inhibit the protein synthesis reaction using the extract solution, and components (e.g., ribosome, aminoacyl tRNA synthetase, various translation factors and the like) essential for the protein synthesis reaction in the *Bombyx mori* L. tissue may be taken into liquid fibroin. These components are difficult to be extracted, and as a result, the amounts of the essential components contained in the extract solution may decrease to lower the amount of protein synthesis. In addition, contamination with liquid fibroin causes higher viscosity of the extract solution itself, which in turn makes progress of the protein synthesis reaction difficult and may degrade the operability.

Figure 2:
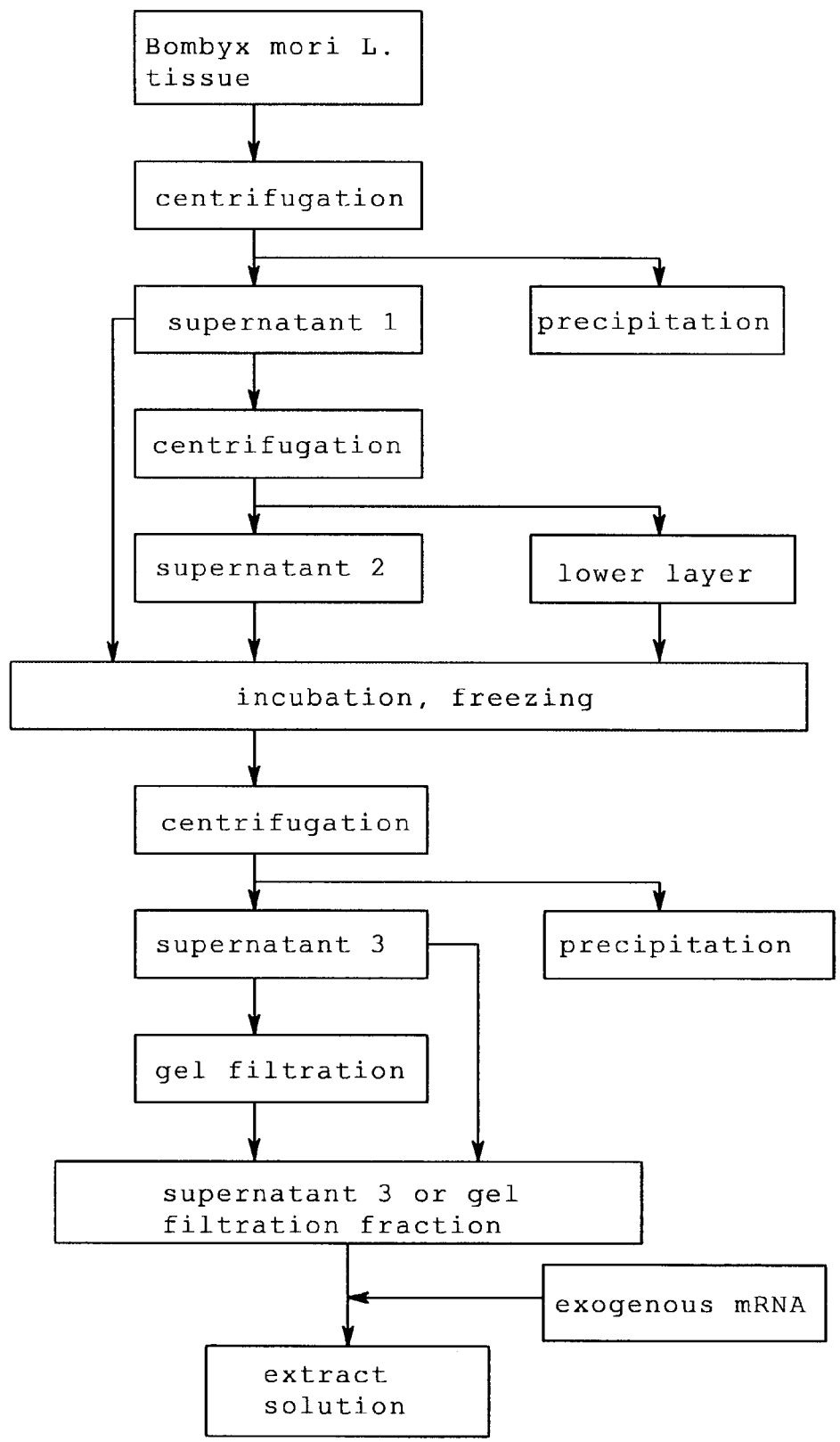
FIG. 2 is a flow chart showing preparation method 4 of the extract solution of the present invention in a simplified manner.

FIG. 2 is a flow chart showing the preparation method 4 in a simplified manner.

To be specific, the above-mentioned extraction is performed using a solution for extraction (pH 4–10), centrifugal separation is applied once as mentioned above to give a supernatant (the above-mentioned supernatant 1), the supernatant (the above-mentioned supernatant 2) obtained by centrifugal separation applied again or the lower layer obtained by centrifugal separation applied again is incubated and frozen. After thawing, an exogenous mRNA is added to the supernatant (hereinafter to be referred to as "supernatant 3") obtained by centrifugal separation to give an extract solution. Alternatively, an exogenous mRNA is added to the filtrate (fraction having an absorbance at 280 nm of not less than 10) obtained by gel filtration of the supernatant 3 to give an extract solution.

According to the preparation method 4, a solution for extraction having a pH of 4–10 is used to solidify liquid fibroin during extraction from the *Bombyx mori* L. tissue, and as a result of which, an extract solution free of liquid fibroin is prepared. Moreover, by a treatment for incubation of the above-mentioned supernatant 1, supernatant 2 or the lower layer and freezing, solidification of the liquid fibroin can be advanced and liquid fibroin can be effectively removed. In addition, the components essential for protein synthesis reaction, which have been taken into the liquid fibroin, can be efficiently extracted.

When an extract solution is prepared by the above-mentioned preparation method 4, a solution for extraction has pH 4–10, preferably pH 6–8, more preferably pH 6–7. When a solution for extraction having a pH of less than 4 is used, the components essential for protein synthesis reaction to be mentioned below may be denatured. When a solution for extraction having a pH exceeding 10 is used, the components essential for protein synthesis reaction may be denatured as mentioned above, and liquid fibroin may not be solidified.

The conditions for incubation of supernatant 1, supernatant 2 or the above-mentioned lower layer are free of any particular limitation, and the conditions conventionally employed generally by those of ordinary skill in the art may be used. The temperature of incubation is preferably not higher than 40° C., more preferably not higher than 30° C. When the temperature exceeds 40° C., the above-mentioned components essential for protein synthesis reaction may be denatured. The period of incubation is preferably not longer than 24 hr, more preferably not longer than 6 hr. When the period of incubation exceeds 24 hr, the components essential for protein synthesis reaction may be denatured.

The freezing after the above-mentioned incubation may be performed under the conditions conventionally employed generally by those of ordinary skill in the art and is free of any particular limitation, with preference given to freezing at not higher than −10° C., more preferably not higher than −20° C. When frozen at a temperature higher than −10° C., the above-mentioned components essential for protein synthesis reaction are tend to be denatured. The time of freezing is preferably not longer than 72 hr, more preferably not longer than 48 hr. Freezing over 72 hr is useless because liquid fibroin has been already solidified and further solidification is not expected.

The conditions of centrifugal separation after thawing are also free of any particular limitation, and, for example, the above-mentioned conditions of 10000×g–50000×g, 0° C.–10° C., 10 min–60 min may be employed. An exogenous mRNA may be directly added to the supernatant (supernatant 3) obtained by the centrifugal separation, or the supernatant 3 is subjected to gel filtration and a fraction having an absorbance at 280 nm of not less than 10 is separated and taken from the filtrate after gel filtration and exogenous mRNA is added to the obtained liquid. When the above-mentioned gel filtration and separation of fraction are to be performed, they are performed in the same manner as above. When the exogenous mRNA is added, the content of the exogenous mRNA should be within the above-mentioned preferable range as an extract solution for cell-free protein synthesis of the present invention. That is, it is preferably added to the extract to achieve a proportion of 1 µg/mL–10 mg/mL, more preferably 15 µg/mL–1700 µg/mL, in the extract solution.

To obtain an extract solution containing a desired amount of the above-mentioned extract, extraction of a plural number of Bombyx mori L. bodies is generally necessary. The number of Bombyx mori L. larvae to be subjected to the extraction varies depending on the condition and interindividual difference found in Bombyx mori L. to be used. For example, as larva approaches the time of cocoon formation, however, a smaller number of Bombyx mori L. larvae suffice for obtaining the same amount of extract due to maturation of the tissues. Because the silk gland particularly remarkably grows daily in Bombyx mori L. larva at laraval stage 5, for example, the same amount obtained from about 30 Bombyx mori L. larvae at day 1 in the laraval stage 5 can be obtained from about 6 or 7 Bombyx mori L. larvae at day 7 in the laraval stage 5.

It is preferable that the extract solution for cell-free protein synthesis of the present invention be obtained by the above-mentioned preparation method, because the afore-mentioned advantages are afforded, but it does not need to be always obtained by the above-mentioned preparation method.

The present invention also provides a liquid composition for cell-free protein synthesis, which contains at least an extract derived from a Bombyx mori L. tissue and a protease inhibitor. The extract derived from a Bombyx mori L. tissue and the protease inhibitor contained in this liquid composition is the same as those mentioned above with regard to the extract solution of the present invention. The liquid composition of the present invention preferably also contains a potassium salt, a magnesium salt, dithiothreitol and a buffer as mentioned above except that the exogenous mRNA is not contained. When cell-free protein synthesis reaction is performed using such liquid composition, it is performed in the same manner as preparation of the reaction mixture using an extract solution to be mentioned below, except further addition of exogenous mRNA to the reaction mixture.

The present invention also provides a method for cell-free protein synthesis using the above-mentioned extract solution. The reaction mixture to be used for the protein synthesis is free of any particular limitation as long as it is conventionally used in the field of cell-free protein synthesis.

The above-mentioned reaction mixture is preferably prepared such that the extract solution of the present invention is contained in a proportion of 10(v/v)%–80(v/v)%, particularly 30(v/v)%–60(v/v)%.

That is, an extract derived from a Bombyx mori L. tissue of 0.1 mg/mL–160 mg/mL, more preferably 3 mg/mL–60 mg/mL, in a protein concentration, is contained relative to the entirety of the above-mentioned reaction mixture. When the content of the extract is less than 0.1 mg/mL or above 160 mg/mL in a protein concentration, the synthesis rate of the protein tends to become lower.

An exogenous mRNA is preferably contained in a proportion of 0.1 µg/mL–8 mg/mL, preferably 1 µg/mL–1000 µg/mL, more preferably 10 µg/mL–500 µg/mL, relative to the entirety of the reaction mixture. When the content of mRNA is less than 1 µg/mL or above 1000 µg/mL, the synthesis rate of the protein tends to become lower.

Generally, the above-mentioned reaction mixture contains, as components other than the above-mentioned extract solution, at least potassium salt, magnesium salt, DTT, adenosine 5'-triphosphate, guanosine 5'-triphosphate, creatine phosphate, creatine kinase, amino acid component, RNase inhibitor, tRNA and buffer. This realizes a reaction mixture for cell-free protein synthesis, which is capable of synthesis of a large amount of a protein in a short time.

As the potassium salt in the reaction mixture, various potassium salts described above as a component of extract solution, preferably potassium acetate, can be preferable used. The potassium salt is preferably contained in a proportion of 10 mM–500 mM, more preferably 50 mM–150 mM, from the same aspect of the potassium salt in the aforementioned extract solution.

As the magnesium salt in the reaction mixture, various magnesium salts described above as a component of extract solution, preferably magnesium acetate, can be preferably used. The magnesium salt is preferably contained in a proportion of 0.1 mM–10 mM, more preferably 0.5 mM–3 mM, from the same aspect of the magnesium salt in the aforementioned extract solution.

DTT is preferably contained in the reaction mixture in a proportion of 0.1 mM–10 mM, more preferably 0.2 mM–5 mM, from the same aspect of DTT in the aforementioned extract solution.

The adenosine 5′-triphosphate (hereinafter sometimes to be referred to as "ATP") is preferably contained in the reaction mixture in a proportion of 0.01 mM–10 mM, more preferably 0.1 mM–5 mM, in view of the rate of protein synthesis. When ATP is contained in a proportion of less than 0.01 mM or above 10 mM, the synthesis rate of the protein tends to become lower.

The guanosine 5′-triphosphate (hereinafter sometimes to be referred to as "GTP") is preferably contained in the reaction mixture in a proportion of 0.01 mM–10 mM, more preferably 0.1 mM–5 mM, in view of the rate of protein synthesis. When GTP is contained in a proportion of less than 0.01 mM or above 10 mM, the synthesis rate of the protein tends to become lower.

The creatine phosphate in the reaction mixture is a component for continuous synthesis of protein and added for regeneration of ATP and GTP. The creatine phosphate is preferably contained in the reaction mixture in a proportion of 1 mM–200 mM, more preferably 10 mM–100 mM, in view of the rate of protein synthesis. When creatine phosphate is less than 1 mM, sufficient amounts of ATP and GTP may not be regenerated easily. As a result, the rate of protein synthesis tends to become lower, and when creatine phosphate exceeds 200 mM, it acts as an inhibitory substance and the synthesis rate of the protein tends to become lower.

The creatine kinase in the reaction mixture is a component for continuous synthesis of protein and added along with creatine phosphate for regeneration of ATP and GTP. The creatine kinase is preferably contained in the reaction mixture in a proportion of 1 µg/mL–1000 µg/mL, more preferably 10 µg/mL–500 µg/mL, in view of the rate of protein synthesis. When creatine kinase is less than 1 µg/mL, regeneration of sufficient amounts of ATP and GTP becomes difficult. As a result, the rate of protein synthesis tends to become lower, and when creatine kinase exceeds 1000 µg/mL, it acts as an inhibitory substance and the synthesis rate of the protein tends to become lower.

The amino acid component in the reaction mixture contains at least 20 kinds of amino acids, i.e., valine, methionine, glutamic acid, alanine, leucine, phenylalanine, glycine, proline, isoleucine, tryptophan, asparagine, serine, threonine, histidine, aspartic acid, tyrosine, lysine, glutamine, cystine and arginine. This amino acid includes radioisotope-labeled amino acid. Where necessary, modified amino acid may be contained. The amino acid component generally contains almost the same amount of various kinds of amino acids.

In the present invention, the above-mentioned amino acid component is preferably contained in the reaction mixture in a proportion of 1 µM–1000 µM, more preferably 10 µM–200 µM, in view of the rate of protein synthesis. When the amount of the amino acid component is less than 1 µM or above 1000 µM, the synthesis rate of the protein tends to become lower.

The RNase inhibitor is added to this reaction mixture to prevent RNase, which is derived from Bombyx mori L. and contaminating the extract solution, from undesirably digesting mRNA and tRNA, thereby preventing synthesis of protein, during cell-free protein synthesis of the present invention. It is preferably contained in the reaction mixture in a proportion of 0.1 U/µL µM–100 U/µL, more preferably 1 U/µL–10 U/µL. When the amount of the RNase inhibitor is less than 0.1 U/µL, the degradation activity of RNase often cannot be suppressed sufficiently, and when the amount of the RNase inhibitor exceeds 100 U/µL, the protein synthesis reaction is tends to be inhibited.

The tRNA in the reaction mixture contains almost the same amount of tRNAs corresponding to the above-mentioned 20 kinds of amino acids. In the present invention, tRNA is preferably contained in the reaction mixture in a proportion of 1 µg/mL–1000 µg/mL, more preferably 10 µg/mL–500 µg/mL, in view of the rate of the protein synthesis. When the amount of the tRNA is less than 1 µg/mL or exceeds 1000 µg/mL, the rate of protein synthesis tends to become lower.

The buffer to be contained in the reaction mixture is preferably similar to those used for the aforementioned extract solution of the present invention, and the use of HEPES-KOH (pH 6–8) is preferable for the same reasons. The buffer is preferably contained in the amount of 5 mM–200 mM, more preferably 10 mM–50 mM, from the same view as in the aforementioned buffer contained in extract solution.

The above-mentioned reaction mixture more preferably contains a glycerol. When glycerol is added, the components essential for protein synthesis can be advantageously stabilized in the protein synthesis reaction. When glycerol is added, the amount is generally 5(v/v)%–20(v/v)%.

Moreover, the above-mentioned reaction mixture preferably contains ethylene glycol bis(2-aminoethylether)tetraacetic acid (hereinafter sometimes to be referred to as "EGTA"). When EGTA is contained, EGTA forms chelate with a metal ion in the extract solution to inactivate ribonuclease, protease and the like. This in turn inhibits decomposition of the components essential for protein synthesis of the present invention. EGTA is preferably contained in the amount of 0.01 mM–10 mM, more preferably 0.1 mM–5 mM, because the above-mentioned decomposition inhibitory capability can be preferably exhibited. When EGTA is less than 0.01 mM, decomposition of essential components cannot be suppressed sufficiently. When it exceeds 10 mM, the protein synthesis reaction tends to be inhibited.

The reaction mixture to be used for the cell-free protein synthesis method of the present invention is preferably realized to contain, besides 30(v/v)%–60(v/v)% of the above-mentioned extract solution, 50 mM–150 mM of potassium acetate, 0.5 mM–3 mM of magnesium acetate, 0.2 mM–5 mM of DTT, 5(v/v)%–20(v/v)% of glycerol, 0.1 mM–5 mM of ATP, 0.1 mM–5 mM of GTP, 10 mM–100 mM of creatine phosphate, 10 µg/mL–500 µg/mL of creatine kinase, 10 µM–200 µM of amino acid component, 1 U/µL–10 U/µL of RNase inhibitor, 10 µg/mL–500 µg/mL of tRNA, 10 µg/mL–500 µg/mL of mRNA and 10 mM–50 mM of HEPES-KOH (pH 6–8). In addition to the above, it is more preferably realized to contain 0.1 mM–5 mM of EGTA.

The cell-free protein synthesis method of the present invention is performed using the above-mentioned reaction mixture containing the extract solution of the present invention in, for example, a conventionally known low temperature thermostat bath.

The reaction temperature is generally within the range of 10° C.–40° C., preferably 20° C.–30° C. When the reaction temperature is lower than 10° C., the synthesis rate of the protein tends to become low and when the reaction temperature exceeds 40° C., the components essential for protein synthesis reaction tend to be denatured.

The time of reaction is generally 1 hr–72 hr, preferably 3 hr–24 hr.

The amount of the protein synthesized by the cell-free protein synthesis method of the present invention can be measured by enzyme activity assay, SDS-PAGE, immunoassay and the like.

The protein synthesized by the cell-free protein synthesis method of the present invention is free of any particular limitation.

EXAMPLES

The present invention is explained in more detail in the following by referring to Examples. These are mere examples and do not limit the present invention in any way.

Example 1

Preparation of Extract Solution Derived from Posterior Silk Gland of *Bombyx mori* L. larvae

*Bombyx mori* L. larvae that reached the laraval stage 5 were sampled every day from day 1 to day 7. From the sampled *Bombyx mori* L., posterior silk gland was enucleated using scissors, pincette and scalpel and posterior silk gland was extracted according to the following steps.

The number of sampled *Bombyx mori* L. larvae and the amount of the enucleated posterior silk gland are shown in Table 1.

TABLE 1

| growing days | number | amount of tissue (g) |
| --- | --- | --- |
| silk gland day 1 | 30 | 1.81 |
| silk gland day 2 | 23 | 2.04 |
| silk gland day 3 | 15 | 2.72 |
| silk gland day 4 | 15 | 3.07 |
| silk gland day 5 | 8 | 1.99 |
| silk gland day 6 | 8 | 2.28 |
| silk gland day 7 | 7 | 1.95 |

For extraction, each posterior silk gland enucleated from *Bombyx mori* L. larvae at laraval stage 5 was frozen with liquid nitrogen, mashed in a mortar frozen at −80° C., and extracted using a solution for extraction of the following composition.

[Composition of Solution for Extraction]

| | |
| --- | --- |
| 20 mM | HEPES-KOH (pH 7.4) |
| 100 mM | potassium acetate |
| 2 mM | magnesium acetate |
| 2 mM | DTT |
| 0.5 mM | PMSF |

After extraction, the obtained liquid product was subjected to centrifugal separation in a centrifuge (himac CR20B3 (manufactured by Hitachi Koki Co., Ltd.)) under the conditions of 30000×g, 30 min, 4° C.

After centrifugal separation, only the supernatant was isolated and subjected again to centrifugal separation under the conditions of 30000×g, 10 min, 4° C. After centrifugal separation, only the supernatant was isolated. A solution for extraction containing 20% glycerol was applied to a desalting column PD-10 (manufactured by Amersham Biosciences) to equilibrate the column, the supernatant was fed and eluted with the above-mentioned solution for extraction for gel filtration.

The fraction of the filtrate after gel filtration was measured for an absorbance at 280 nm using a spectrophotometer (Ultrospec 3300pro, manufactured by Amersham Biosciences) and a fraction having an absorbance of not less than 10 was separated and taken. Thereto was added 40 µg/mL of exogenous mRNA to give an extract solution for cell-free protein synthesis derived from the posterior silk gland of *Bombyx mori* L. larvae at laraval stage 5. As the exogenous mRNA, mRNA encoding luciferase (luciferase control RNA, manufactured by Promega) was used.

The obtained extract solution was measured for protein concentration using a BCA Protein assay Kit (manufactured by PIERCE). First, a sample (0.1 mL) was added to a reaction reagent (2 mL) and they were reacted at 37° C. for 30 min and absorbance at 562 nm was measured using a spectrophotometer (Ultrospec 3300 pro, manufactured by Amersham Biosciences). BSA was used as a control and a calibration curve was drawn. The protein concentration of each extract solution thus obtained was as follows.

TABLE 2

| growing days | protein concentration (mg/mL) |
| --- | --- |
| silk gland day 1 | 8.9 |
| silk gland day 2 | 11.5 |
| silk gland day 3 | 14.6 |
| silk gland day 4 | 17.5 |
| silk gland day 5 | 7.9 |
| silk gland day 6 | 18.7 |
| silk gland day 7 | 19.3 |

The average time necessary for one skilled person to prepare the extract solution by the above-mentioned preparation method was about 2 hr.

Example 2

Preparation of Extract Solution Derived from Fat Body of *Bombyx mori* L. larvae In the same manner as in Example 1 except that fat body was enucleated from *Bombyx mori* L. larvae sampled every day from day 1 to day 7, which reached laraval stage 5, and an extract solution containing the fat body of each day was prepared.

The number of the sampled *Bombyx mori* L. larvae and the amount of the enucleated fat body are shown in Table 3 and the protein concentration of each extract solution obtained is shown in Table 4.

TABLE 3

| growing days | number | amount of tissue (g) |
| --- | --- | --- |
| fat body day 1 | 30 | 1.94 |
| fat body day 2 | 23 | 1.87 |
| fat body day 3 | 15 | 2.10 |
| fat body day 4 | 15 | 1.51 |
| fat body day 5 | 8 | 1.83 |
| fat body day 6 | 8 | 2.52 |
| fat body day 7 | 7 | 2.11 |

TABLE 4

| growing days | protein concentration (mg/mL) |
| --- | --- |
| fat body day 1 | 13.3 |
| fat body day 2 | 16.5 |
| fat body day 3 | 28.3 |
| fat body day 4 | 31.6 |
| fat body day 5 | 29.0 |

TABLE 4-continued

| growing days | protein concentration (mg/mL) |
|---|---|
| fat body day 6 | 56.9 |
| fat body day 7 | 51.9 |

The average time necessary for one skilled person to prepare the extract solution by the above-mentioned preparation method was about 2 hr.

Experimental Example 1

Protein Synthesis by Cell-free System Using Extract Solutions of Examples 1 and 2

Using extract solution obtained in the above-mentioned Examples 1 and 2, a reaction mixture having the following composition was prepared.

[Composition of the Reaction Mixture]

| 50 (v/v) % | extract solution (exogenous mRNA in the reaction mixture: 20 µg/mL) |
|---|---|
| 30 mM | HEPES-KOH (pH 7.4) |
| 100 mM | potassium acetate |
| 1 mM | magnesium acetate |
| 3 mM | DTT |
| 10 (v/v) % | glycerol |
| 0.5 mM | ATP |
| 0.1 mM | GTP |
| 25 mM | creatine phosphate |
| 200 µg/mL | creatine kinase |
| 40 µM | amino acid (20 kinds) |
| 1 U/µL | RNase inhibitor |
| 200 µg/mL | tRNA |

ATP (manufactured by Sigma), GTP (manufactured by Sigma), amino acid (20 kinds) (manufactured by Sigma), RNase inhibitor (manufactured by TAKARA SHUZO CO., LTD.) and tRNA (manufactured by Roche Diagnostics) were respectively used.

Using the prepared reaction mixtures, and low temperature dry block bath MG-1000 (manufactured by TOKYO RIKAKIKAI Co.) as a reaction apparatus, a synthesis reaction of protein (luciferase) was performed by the cell-free system. The amount of the reaction mixture was 25 µL. The reaction temperature was 20° C. and samples were taken for each reaction time and the amount of synthesized luciferase was measured.

The synthesized luciferase was quantified using a luciferase assay kit (E-1500, manufactured by Promega). A reaction mixture (2.5 µL) was added to a luciferase assay reagent (50 µL) and luminescence by luciferase was measured using a luminometer (Turner Designs TD-20/20, manufactured by Promega).

Figure 3:
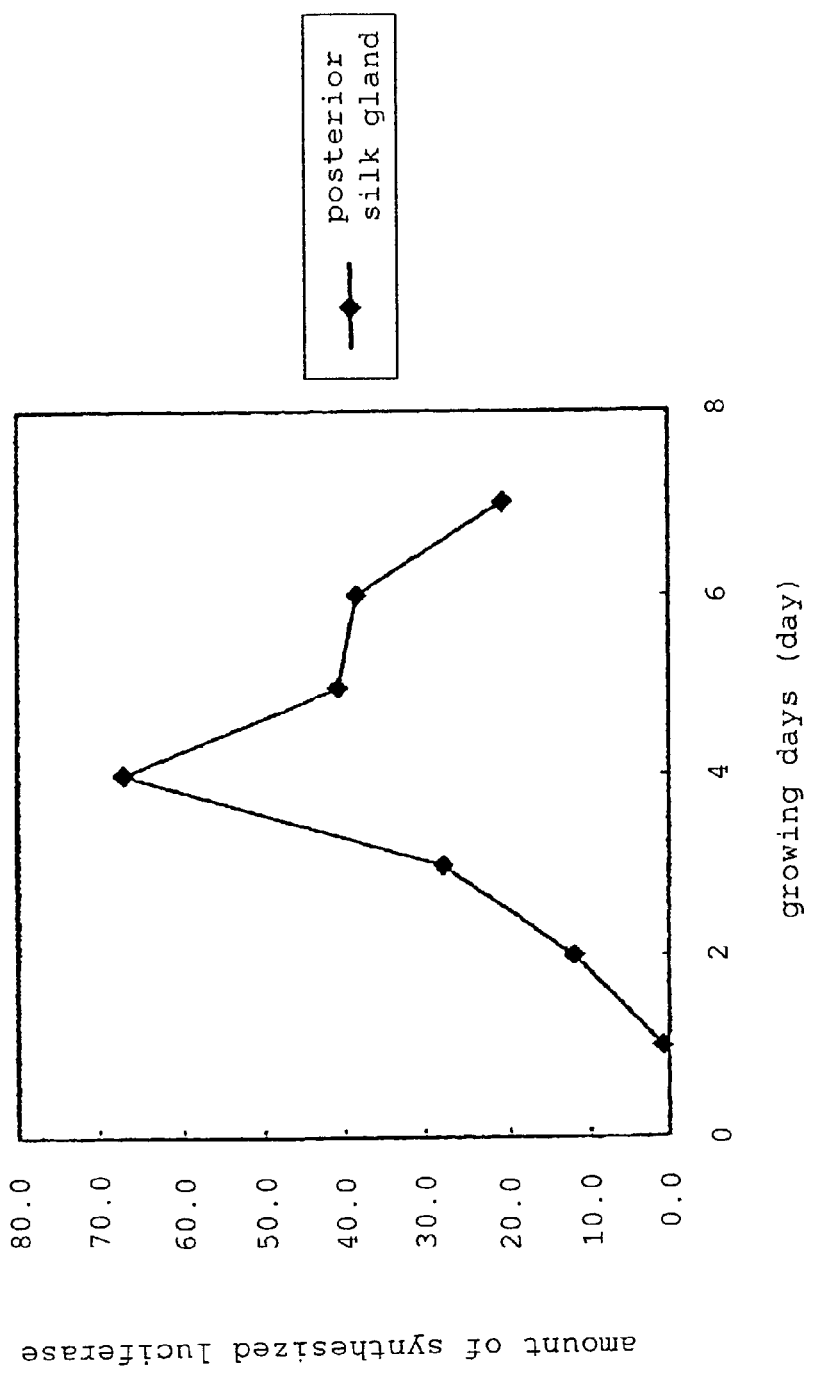
FIG. 3 is a graph showing an amount of luciferase synthesized in each reaction mixture in 2 hr from the start of the reaction using the extract solution of Example 1 (containing the posterior silk gland of *Bombyx mori* L. larvae), wherein the axis of ordinate shows the amount (ng/mL) of synthesized luciferase and the axis of abscissa shows the growing days of *Bombyx mori* L. larvae in laraval stage 5.

FIG. 3 is a graph showing an amount of synthesized luciferase in each reaction mixture in 2 hr from the start of the reaction using the extract solution of Example 1 (containing the posterior silk gland of *Bombyx mori* L. larvae), wherein the axis of ordinate shows the amount (ng/mL) of synthesized luciferase and the axis of abscissa shows the growing days of *Bombyx mori* L. at laraval stage 5.

Figure 4:
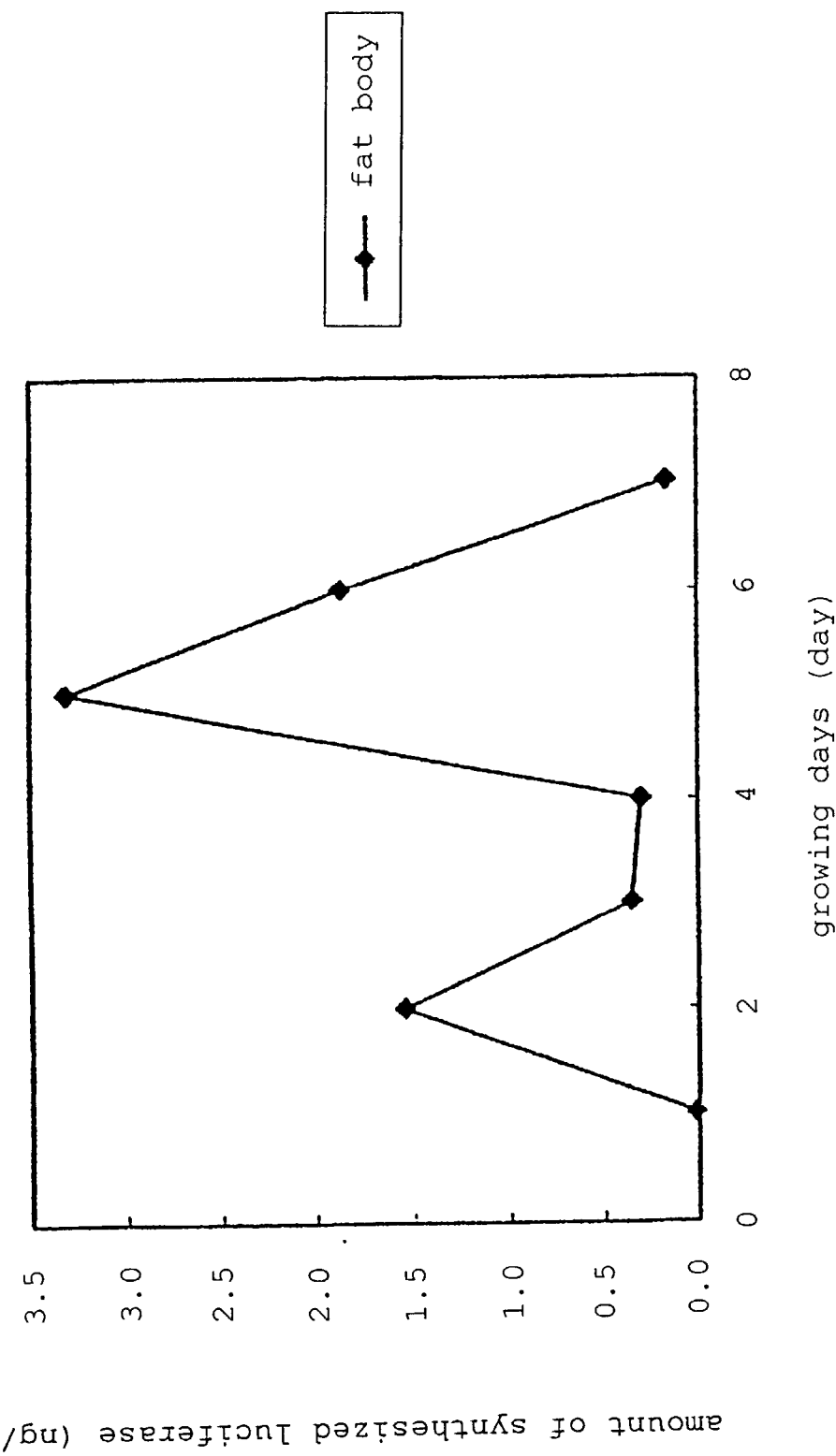
FIG. 4 is a graph showing an amount of luciferase synthesized in each reaction mixture in 2 hr from the start of the reaction using the extract solution of Example 2 (containing the fat body of *Bombyx mori* L. larvae), wherein the axis of ordinate shows the amount (ng/mL) of synthesized luciferase and the axis of abscissa shows the growing days of *Bombyx mori* L. larvae in laraval stage 5.

FIG. 4 is a graph showing an amount of synthesized luciferase in each reaction mixture in 2 hr from the start of the reaction using the extract solution of Example 2 (containing the fat body of *Bombyx mori* L. larvae), wherein the axis of ordinate shows the amount (ng/mL) of synthesized luciferase and the axis of abscissa shows the growing days of *Bombyx mori* L. larvae at laraval stage 5.

Figure 5:
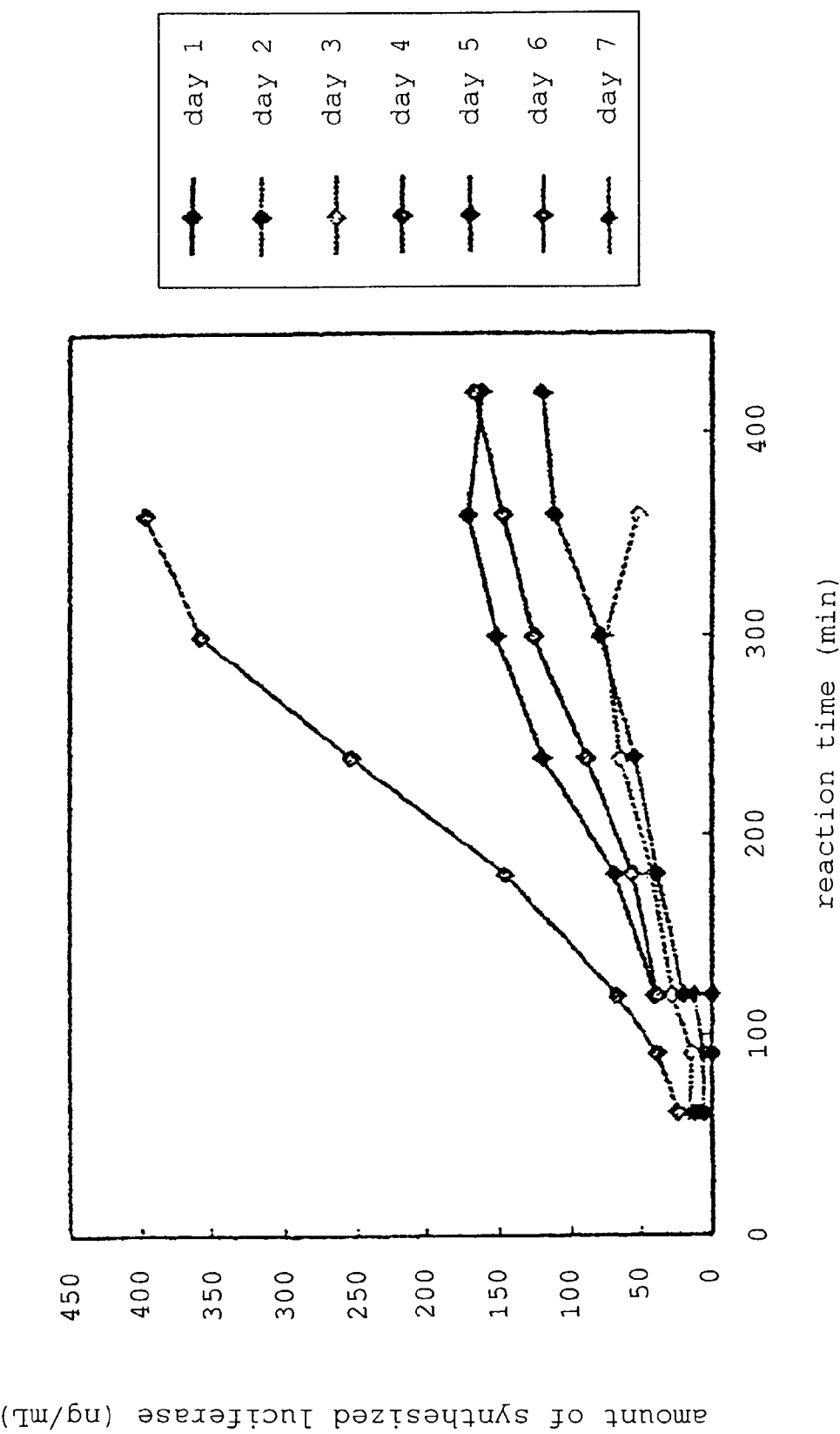
FIG. 5 is a graph showing an amount of luciferase synthesized in each reaction mixture (sample of each day from day 1 to day 7) relative to the reaction time using the extract solution of Example 1, wherein the axis of ordinate shows the amount (ng/mL) of synthesized luciferase and the axis of abscissa shows the reaction time (min).

FIG. 5 is a graph showing an amount of synthesized luciferase in each reaction mixture (sample of each day from day 1 to day 7) relative to the reaction time using the extract solution of Example 1, wherein the axis of ordinate shows the amount (ng/mL) of synthesized luciferase and the axis of abscissa shows the reaction time (min).

As shown in FIG. 5, the reaction mixture for cell-free protein synthesis, which was prepared using an extract solution containing an extract derived from the posterior silk gland of *Bombyx mori* L. larvae at day 4 of laraval stage 5, showed continuous reaction for 6 hr and synthesis of 397.4 ng/mL of luciferase. Moreover, the reaction using this reaction mixture synthesized 657.4 ng/mL of luciferase in 23 hr.

Experimental Example 2

The effect of each amount of the component added on the cell-free protein synthesis reaction using the extract solution of Example 1 was examined. The optimal composition of the reaction mixture was as follows.

[Composition of the Reaction Mixture]

| 50 (v/v) % | extract solution (containing posterior silk gland of Bombyx mori L. larvae at day 4 of laraval stage 5) (exogenous mRNA in the reaction mixture: 40 µg/mL) |
|---|---|
| 30 mM | HEPES-KOH (pH 7.4) |
| 75 mM | potassium acetate |
| 1.5 mM | magnesium acetate |
| 0.5 mM | DTT |
| 10 (v/v) % | glycerol |
| 0.5 mM | ATP |
| 0.5 mM | GTP |
| 0.25 mM | EGTA |
| 25 mM | creatine phosphate |
| 200 µg/mL | creatine kinase |
| 40 µM | amino acid (20 kinds) |
| 2 U/µL | RNase inhibitor |
| 200 µg/mL | tRNA |

In the same manner as in the above-mentioned Experimental Example 1 except that the reaction mixture of the above-mentioned optimized composition was used and the temperature of the reaction was set to 25° C., luciferase was synthesized.

Figure 6:
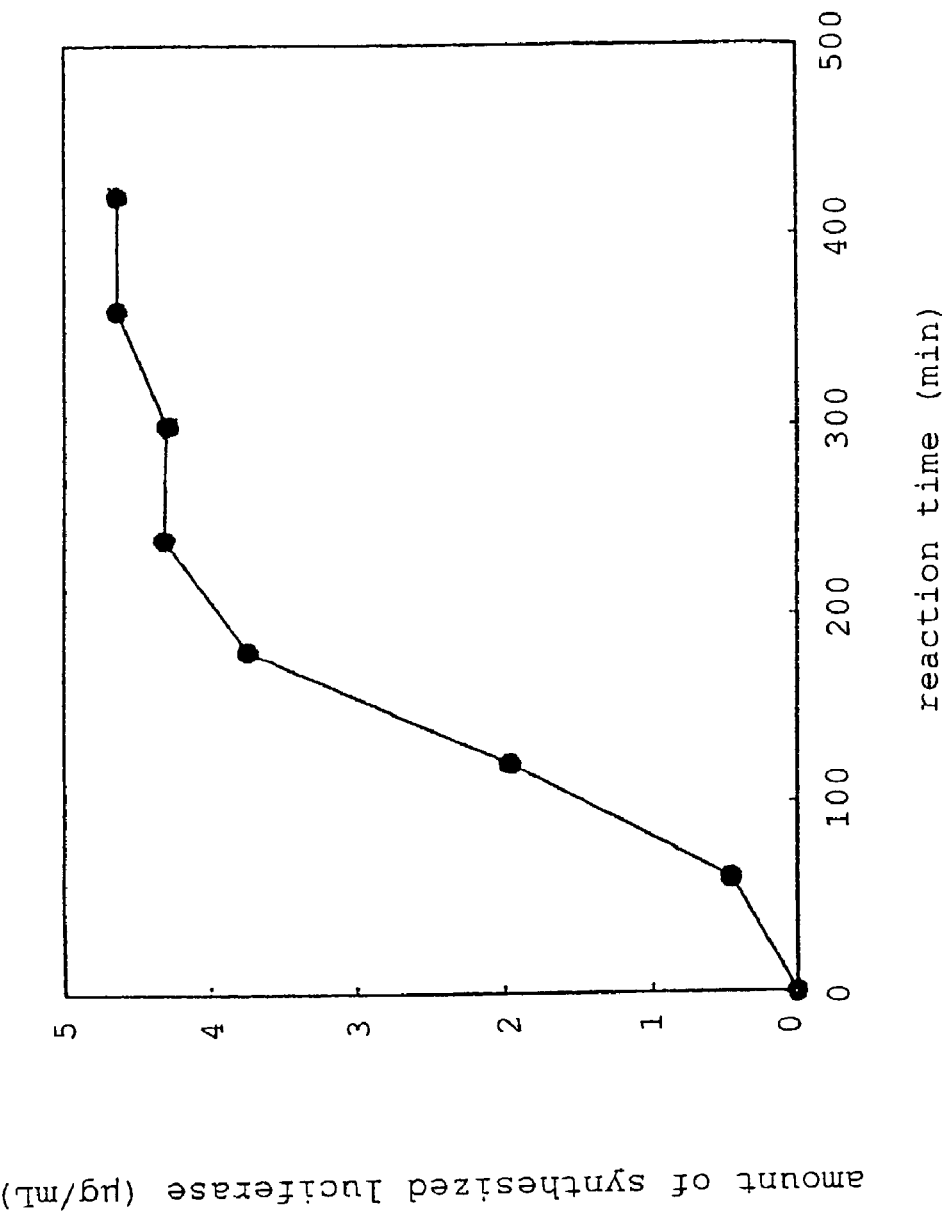
FIG. 6 is a graph showing an amount of synthesized luciferase relative to the reaction time in the reaction mixture having an optimized composition, wherein the axis of ordinate shows the amount (μg/mL) of synthesized luciferase and the axis of abscissa shows the reaction time (min).

FIG. 6 is a graph showing an amount of synthesized luciferase relative to the reaction time of the reaction mixture having an optimized composition, wherein the axis of ordinate shows the amount (µg/mL) of synthesized luciferase and the axis of abscissa shows the reaction time (min).

As shown in FIG. 6, the reaction mixture having an optimized composition showed a continuous reaction for 4 hr and synthesis of 4.6 µg/mL of luciferase.

Example 3

Preparation of Extract Solution Derived from Embryo of *Bombyx mori* L.

The eggs of *Bombyx mori* L. at day 0, day 2, day 5 and day 7 incubated at 25° C. after laying were taken by 2 g each and an extract solution was prepared in the same manner as in Example 1. The protein concentration of each extract solution obtained was as follows.

TABLE 5

| days of incubation | protein concentration (mg/mL) |
| --- | --- |
| 0 | 55.5 |
| 2 days | 65.7 |
| 5 days | 46.4 |
| 7 days | 27.0 |

The average time necessary for one skilled person to prepare the extract solution by the above-mentioned preparation method was about 1.5 hr.

Experimental Example 3

Protein Synthesis by Cell-free System Using Extract Solution of Example 3

In the same manner as in the above-mentioned Experimental Example 1 except that the extract solution obtained in the above-mentioned Example 3 was used, a reaction mixture having the same composition was prepared and subjected to protein (luciferase) synthesis by the cell-free system.

As a result, the extract solution derived from the embryo at day 2 showed synthesis of 16 ng/mL of luciferase.

Example 4

Preparation of Extract Solution Derived from Posterior Silk Gland of *Bombyx mori* L. larvae

*Bombyx mori* L. larvae that reached day 5 of the laraval stage 5 were sampled. From the sampled *Bombyx mori* L., the posterior silk gland was enucleated using scissors, pincette and scalpel and posterior silk gland was extracted according to the following steps.

For extraction, each posterior silk gland enucleated from *Bombyx mori* L. larvae at day 5 of laraval stage 5 was frozen with liquid nitrogen, mashed in a mortar frozen at −80° C., and extracted using a solution for extraction of the following composition.

[Composition of solution for extraction]

| 20 mM | HEPES-KOH (pH 7.0) |
| --- | --- |
| 100 mM | potassium acetate |
| 2 mM | magnesium acetate |
| 1 mM | DTT |
| 0.5 mM | PMSF |

After extraction, the obtained liquid product was subjected to centrifugal separation in a centrifuge (himac CR20B3 (manufactured by Hitachi Koki Co., Ltd.)) under the conditions of 30000×g, 10 min, 4° C. After centrifugal separation, only the supernatant was isolated and subjected again to centrifugal separation under the conditions of 30000×g, 30 min, 4° C. to isolate the lower layer. The lower layer was incubated at room temperature (25° C.) for 6 hr and frozen for one day at −80° C.

After thawing the frozen lower layer at room temperature, it was subjected to centrifugal separation at 22000×g, 60 min, 4° C.

After centrifugal separation, only the supernatant was isolated. To the obtained supernatant was added 320 µg/mL of exogenous mRNA to give an extract solution for cell-free protein synthesis derived from the posterior silk gland of *Bombyx mori* L. larvae at laraval stage 5. As an exogenous mRNA, an mRNA encoding luciferase (luciferase control RNA, manufactured by Promega) was used. The absorbance at 280 nm of this extract solution as measured using a spectrophotometer (Ultrospec 3300pro, manufactured by Amersham Biosciences) was 62.4.

The average time necessary for one skilled person to prepare the extract solution by the above-mentioned preparation method was about 24 hr.

Experimental Example 4

Protein Synthesis by Cell-free System Using Extract Solution of Example 4

A reaction mixture having the following composition was prepared using the extract solution obtained in the above-mentioned Example 4, and in the same manner as in Experimental Example 1, luciferase was synthesized.

[Composition of the Reaction Mixture]

| 50 (v/v) % | extract solution (exogenous mRNA in the reaction mixture: 160 µg/mL) |
| --- | --- |
| 30 mM | HEPES-KOH (pH 7.4) |
| 100 mM | potassium acetate |
| 1.5 mM | magnesium acetate |
| 0.5 mM | DTT |
| 10% (v/v) % | glycerol |
| 0.5 mM | ATP |
| 0.5 mM | GTP |
| 0.25 mM | EGTA |
| 25 mM | creatine phosphate |
| 200 µg/mL | creatine kinase |
| 40 µM | amino acid (20 kinds) |
| 2 U/µL | RNase inhibitor |
| 200 µg/mL | tRNA |

Figure 7:
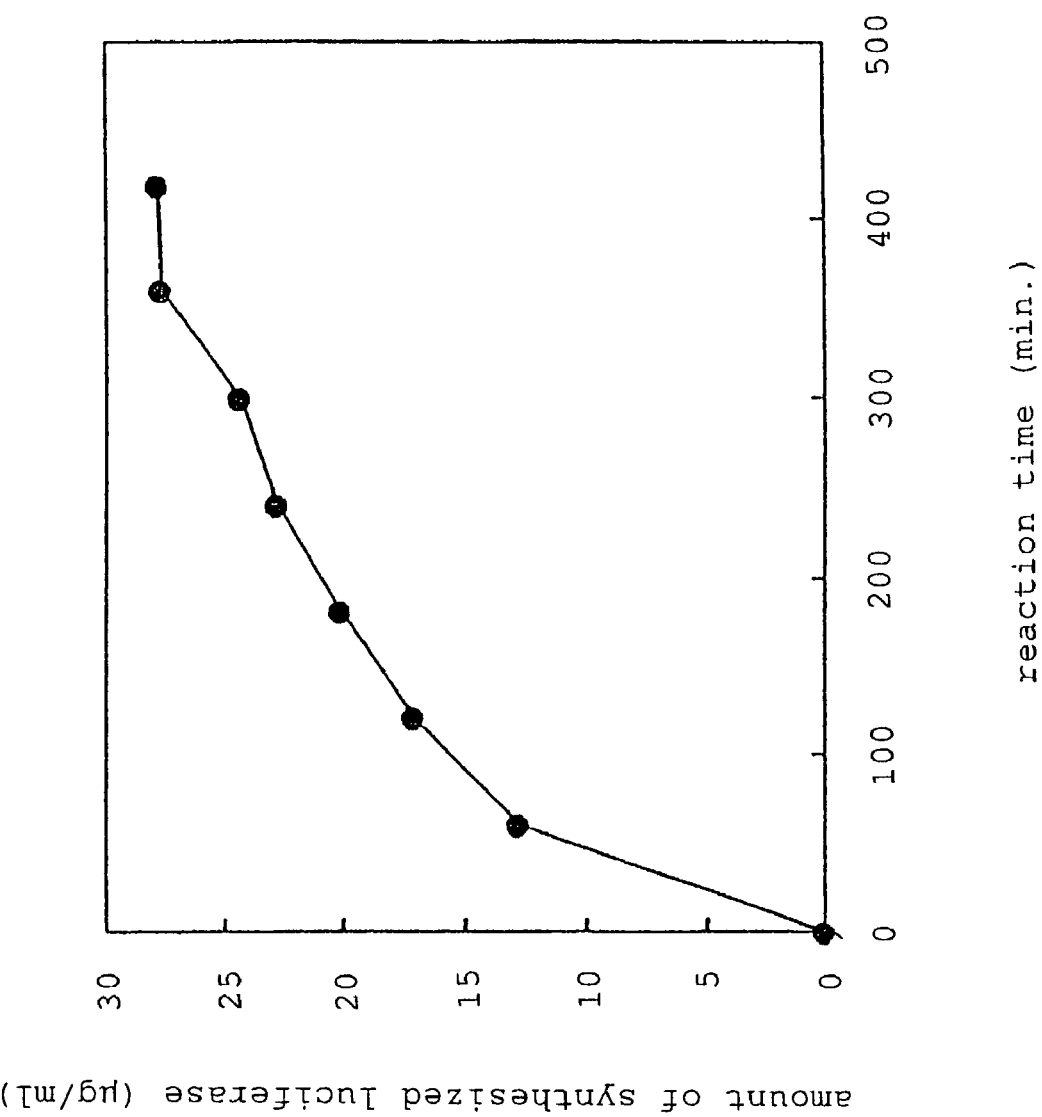
FIG. 7 is a graph showing an amount of synthesized luciferase relative to the reaction time in the reaction mixture using the extract solution of Example 4 (containing the posterior silk gland of *Bombyx mori* L. larvae), wherein the axis of ordinate shows the amount (μg/mL) of synthesized luciferase and the axis of abscissa shows the reaction time (min).

FIG. 7 is a graph showing an amount of synthesized luciferase in a reaction mixture using the extract solution of Example 4 (containing the posterior silk gland of *Bombyx mori* L. larvae) relative to the reaction time, wherein the axis of ordinate shows the amount (µg/mL) of synthesized luciferase and the axis of abscissa shows the reaction time (min).

As shown in FIG. 7, the reaction mixture for cell-free protein synthesis, which was prepared using an extract solution containing an extract derived from the posterior silk gland of *Bombyx mori* L. larvae at day 5 of laraval stage 5 showed continuous reaction for 7 hr and synthesis of 28 µg/mL of luciferase.

Example 5

Preparation of Extract Solution Derived from Posterior Silk Gland of *Bombyx mori* L. larvae

*Bombyx mori* L. larvae that reached day 4 of laraval stage 5 were sampled. From the sampled *Bombyx mori* L., posterior silk gland was enucleated using scissors, pincette and scalpel and posterior silk gland was extracted according to the following steps.

For extraction, the posterior silk gland enucleated from *Bombyx mori* L. larvae at day 4 of laraval stage 5 was frozen with liquid nitrogen, mashed in a mortar frozen at −80° C., and extracted using a solution for extraction of the following composition.

[Composition of Solution for Extraction]

| | |
|---|---|
| 20 mM | HEPES-KOH (pH 7.4) |
| 100 mM | potassium acetate |
| 2 mM | magnesium acetate |
| 1 mM | DTT |

After extraction, the obtained liquid product was subjected to centrifugal separation in a centrifuge (himac CR20B3 (manufactured by Hitachi Koki Co., Ltd.)) under the conditions of 30000×g, 10 min, 4° C.

After centrifugal separation, only the supernatant was isolated and subjected to centrifugal separation again under the conditions of 30000×g, 30 min, 4° C. After centrifugal separation, only the supernatant was isolated.

A solution for extraction containing 20% glycerol was applied to a desalting column PD-10 (manufactured by Amersham Biosciences) to equilibrate the column, the supernatant was fed and eluted with the above-mentioned solution for extraction for gel filtration.

The fraction filtrate after gel filtration was subjected to spectrophotometer (Ultrospec 3300pro, manufactured by Amersham Biosciences) and a fraction having an absorbance at 280 nm of not less than 10 was separated and taken. Thereto was added 80 μg/mL of exogenous mRNA to give an extract solution for cell-free protein synthesis, which is derived from the posterior silk gland of Bombyx mori L. larvae at laraval stage 5. As the exogenous mRNA, mRNA encoding luciferase (luciferase control RNA, manufactured by Promega) was used.

The average time necessary for one skilled person to prepare the extract solution by the above-mentioned preparation method was about 2 hr.

Experimental Example 5

Protein Synthesis by Cell-free System Using Extract Solution of Example 5

Using the extract solution obtained in the above-mentioned Example 5, a reaction mixture of the following composition was prepared, and in the same manner as in Experimental Example 1, luciferase was synthesized.

[Composition of the Reaction Mixture]

| | | |
|---|---|---|
| 50 (v/v) % | extract solution (exogenous mRNA in the reaction mixture: 40 μg/mL) | |
| 30 mM | HEPES-KOH (pH 7.4) | |
| 100 mM | potassium acetate | |
| 1.5 mM | magnesium acetate | |
| 0.5 mM | DTT | |
| 10% (v/v) % | glycerol | |
| 0.5 mM | ATP | |
| 0.5 mM | GTP | |
| 0.25 mM | EGTA | |
| 25 mM | creatine phosphate | |
| 200 μg/ml | creatine kinase | |
| 40 μM | amino acid (20 kinds) | |
| 2 U/μL | RNase inhibitor | |
| 200 μg/ml | tRNA | |

As a result, the amount of protein (luciferase) synthesis without addition of PMSF showed a decrease to 50.2% of the amount obtained upon addition of PMSF.

As is clear from the foregoing explanation, the present invention can provide a novel extract solution for cell-free protein synthesis, which is easy to prepare and is capable of realizing cell-free protein synthesis that can synthesize glycoprotein because of the derivation of eucaryote, a preparation method thereof and protein synthesis method in a cell-free system using the extract solution.

This application is based on application No. 375822/2001 filed in Japan, the contents of which are incorporated hereinto by reference.

What is claimed is:

1. An extract solution for cell-free protein synthesis, which comprises at least an extract derived from a Bombyx mori L. tissue and an exogenous mRNA, wherein the extract solution is prepared by a process comprising at least the steps of:
    providing the Bombyx mori L. tissue,
    freezing the tissue,
    crushing the frozen tissue,
    extracting the crushed frozen tissue with a buffered solution at a pH of 4–10 for extraction to obtain a liquid containing the extract,
    subjecting the liquid to centrifugation to obtain a supernatant, and
    adding to the supernatant the exogenous mRNA to obtain the extract solution for cell-free protein synthesis.

2. The extract solution of claim 1, further comprising a protease inhibitor.

3. The extract solution of claim 2, wherein the protease inhibitor is phenylmethanesulfonyl fluoride.

4. The extract solution of claim 1, wherein a content of the extract derived from a Bombyx mori L. tissue is 1 mg/mL–200 mg/mL in a protein concentration.

5. The extract solution of claim i, wherein the Bombyx mori L. tissue comprises at least a posterior silk gland of Bombyx mori L. larva.

6. The extract solution of claim 1, wherein the Bombyx mori L. tissue comprises at least a fat body of the Bombyx mori L. larva.

7. The extract solution of claim 1, wherein the Bombyx mori L. tissue comprises at least an embryo of Bombyx mori L.

8. The extract solution of claim 2, wherein the Bombyx mori L. tissue comprises at least a posterior silk gland of Bombyx mori L. larva.

9. The extract solution of claim 2, wherein the Bombyx mori L. tissue comprises at least a fat body of Bombyx mori L. larva.

10. The extract solution of claim 2, wherein the Bombyx mori L. tissue comprises at least an embryo of Bombyx mori L.

11. An extract solution for cell-free protein synthesis, which comprises at least an extract derived from a Bombyx mori L. tissue, an exogenous mRNA and a protease inhibitor, wherein the Bombyx mori L. tissue is a posterior silk gland of Bombyx mori L. larva, and the protease inhibitor is phenylmethanesulfonyl fluoride, wherein the extract solution is prepared by a process comprising at least the steps of:
    providing the Bombyx mori L. tissue,
    freezing the tissue,
    crushing the frozen tissue,
    extracting the crushed frozen tissue with a buffered solution at a pH of 4–10 for extraction to obtain a liquid containing the extract,
    subjecting the liquid to centrifugation to obtain a supernatant, and
    adding to the supernatant the exogenous mRNA and the protease inhibitor to obtain the extract solution for cell-free protein synthesis.

12. A liquid composition for cell-free protein synthesis, which comprises at least an extract derived from a *Bombyx mori* L. tissue and a protease inhibitor, wherein the extract solution is prepared by a process comprising at least the steps of:
provinging the *Bombyx mori* L. tissue,
freezing the tissue,
crushing the frozen tissue,
extracting the crushed frozen tissue with a buffered solution at a pH of 4–10 for extraction to obtain a liquid containing the extract,
subjecting the liquid to centrifugation to obtain a supernatant, and
adding to the supernatant the protease inhibitor to obtain the liquid composition for cell-free protein synthesis.

13. A method for cell-free protein synthesis, which comprises subjecting the extract solution of claim 1 and a reaction mixture comprising at least potassium salt, magnesium salt, dithiothreitol, adenosine triphosphate, guanosine triphosphate, creatine phosphate, creatine kinase, amino acids, Rnase inhibitor, tRNA and a buffer, to conditions suitable for protein synthesis to produce the protein.

14. A method for cell-free protein synthesis, which comprises subjecting the extract solution of claim 2 and a reaction mixture comprising at least potassium salt, magnesium salt, dithiothreitol, adenosine triphosphate, guanosine triphosphate, creatine phosphate, creatine kinase, amino acids, Rnase inhibitor, tRNA and a buffer, to conditions suitable for protein synthesis to produce the protein.

15. A method for preparing an extract solution for cell-free protein synthesis, which comprises at least the steps of:
providing the *Bombyx mori* L. tissue,
freezing the tissue,
crushing the frozen tissue,
extracting the crushed frozen tissue with a buffered solution at a pH of 4–10 for extraction to obtain a liquid containing the extract,
subjecting the liquid to centrifugation to obtain a supernatant, and
adding to the supernatant the exogenous mRNA to obtain the extract solution for cell-free protein synthesis.

16. The preparation method of claim 15, wherein the solution for extraction comprises a protease inhibitor.

17. The preparation method of claim 15, wherein the extract derived from a *Bombyx mori* L. tissue obtained by extracting from the *Bombyx mori* L. tissue using a solution for extraction is treated for removing liquid fibroin.

* * * * *